United States Patent
Dinh et al.

(10) Patent No.: US 6,500,977 B1
(45) Date of Patent: Dec. 31, 2002

(54) PROCESS FOR PRODUCING ORGANOSILANES

(75) Inventors: Paul C. Dinh, Midland, MI (US); Dennis E. Phillips, Midland, MI (US); David L. Brandt, Midland, MI (US); William C. Maki, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 09/995,045

(22) Filed: Nov. 27, 2001

(51) Int. Cl.⁷ .................................................. C07F 7/08
(52) U.S. Cl. ........................................................ 556/479
(58) Field of Search ........................................... 556/479

(56) References Cited

U.S. PATENT DOCUMENTS

| | | | |
|---|---|---|---|
| 5,177,236 A | 1/1993 | Seiler et al. | |
| 5,359,111 A * | 10/1994 | Kleyer et al. | 556/479 |
| 5,559,264 A | 9/1996 | Bowman et al. | |
| 5,646,326 A * | 7/1997 | Schuler | 556/479 X |
| 6,153,782 A | 11/2000 | Krauter et al. | |
| 6,169,196 B1 * | 1/2001 | Geisberger et al. | 556/479 |
| 6,177,585 B1 | 1/2001 | Chen et al. | |
| 6,191,297 B1 | 2/2001 | Batz-Sohn et al. | |
| 6,242,630 B1 | 6/2001 | Bade et al. | |
| 6,303,728 B1 * | 10/2001 | Hagimori et al. | 556/479 X |

* cited by examiner

Primary Examiner—Paul F. Shaver
(74) Attorney, Agent, or Firm—Reising, Ethington, Barnes, Kisselle, Learman & McCulloch PC

(57) ABSTRACT

A process for producing an organosilane including reacting an alkene halide with a hydrogen silane in the presence of a hydrosilating catalyst. The alkene halide is present in an amount such that a molar excess of at least 5 moles per one mole of hydrogen silane is maintained.

14 Claims, 1 Drawing Sheet

PROCESS FOR PRODUCING ORGANOSILANES

BACKGROUND OF THE INVENTION

1. Field of the Invention

The invention relates to a process for the preparation of organosilanes in an efficient manner, such that the yield of a preferred product is increased. With more particularity, the invention relates to a process for the preparation of organosilanes in an efficient manner by reacting a molar excess of an alkene halide with a hydrogen silane.

2. Description of the Related Art

Organosilanes may be produced by the reaction of an alkene halide with a hydrogen silane and can be represented by the following equation:

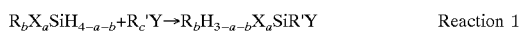

Reaction 1

Where R is selected from the group consisting of alkyls having one to about 20 carbons, cycloalkyls having from 4 to 12 carbons and aryls; X is a halogen; R' is an alkyl having from one to twenty carbons and Y is a halogen; $a=0$ to 3, $b=0$ to 3; and $a+b=1$ to 3.

Particularly useful organosilanes include halopropylorganosilanes that are common intermediate materials in organosilane chemistry.

Halopropylorganosilanes are generally prepared by a catalyzed reaction of an allyl halide with a hydrogen silane in a hydrosilation or hydrosilyation process and can be described by the following general reaction equation:

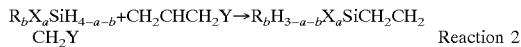

Reaction 2

Where R is selected from the group consisting of alkyls having one to about 20 carbons, cycloalkyls having from 4 to 12 carbons and aryls; X is a halogen; and Y is a halogen; $a=0$ to 3, $b=0$ to 3; and $a+b=1$ to 3.

The hydrosilation reaction is accompanied by an undesired side reaction to produce a by product propylorganosilane and can be described by the following general reaction equation:

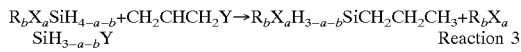

Reaction 3

Where R is selected from the group consisting of alkyls having one to about 20 carbons, cycloalkyls having from 4 to 12 carbons and aryls; X is a halogen; and Y is a halogen; $a=0$ to 3, $b=0$ to 3; and $a+b=1$ to 3.

A common halopropylorganosilane utilized in the chemical industry is chloropropyltrichlorosilane which is produced from the reaction of trichlorosilane and allyl chloride according to the following reaction equation:

Reaction 4

The by product, propyltrichlorosilane is produced from a secondary reaction and can be represented by the following reaction equation:

Reaction 5

It is known in the art that the efficiency of a process for producing halopropylorganosilanes can be improved if the amount of the undesirable by product can be reduced. For example, U.S. Pat. No. 6,242,630 discloses a process for the continuous preparation of halopropylorganosilanes wherein the reaction carried out is a partial reaction of from 10% to 80% on a molar basis of the starting materials. This process requires complex control and monitoring to maintain the process conditions; thereby increasing the costs of the process.

U.S. Pat. No. 5,177,236 discloses a process for the preparation of chloropropyltrichlorosilane from a hydrogen silane and allyl chloride wherein the reaction temperature is maintained at the boiling point of the higher boiling point reactant. The reaction takes place in the presence of a platinum containing carrier material which is located above the reactant mixture. The vapors of the reactant mixture are conducted through a condenser which bypasses the carrier material. The condensate is then passed through the carrier material into the boiling reactant mixture. The condensate formed in the condenser contains a stoichiometric excess of allyl chloride based on the hydrogen silane reaction compound. This process is again complex, and requires a high energy load to vaporize the reactants. The vaporization of the reactants also limits the excess amount of allyl chloride possible for reaction, as an equilibrium will be maintained between the vapor and boiling liquid of allyl chloride. The vaporization of the reactants also limits the amount of excess allyl chloride in that the rate of vaporization of the reactants will limit the amount of allyl chloride in the condensate.

There is, therefore, a need in the art to provide a cost and energy efficient process for the production of a halopropylorganosilane that minimizes the production of an undesired by product.

SUMMARY OF THE INVENTION

The present invention is a process for producing organosilanes including reacting an alkene halide with a hydrogen silane in the presence of a hydrosilating catalyst. The alkene halide and hydrogen silane are maintained in a liquid phase. The alkene halide is present in an amount such that a molar excess of at least 1.1 moles of alkene halide per mole of hydrogen silane is maintained.

The process of the present invention has the advantage of providing a process that does not require complex control or monitoring or require a high energy load to produce the desired product.

The process of the present invention also provides the advantage of increasing the yield of a desired product in relation to the undesired product that results in a higher silicon efficiency and lower process waste.

The process of the present invention has the further advantage of providing a process that has a reaction in a liquid phase utilizing liquid reactants that do not require the use of a high energy load, and are easy to process.

DETAILED DESCRIPTION OF THE INVENTION

Figure 1:
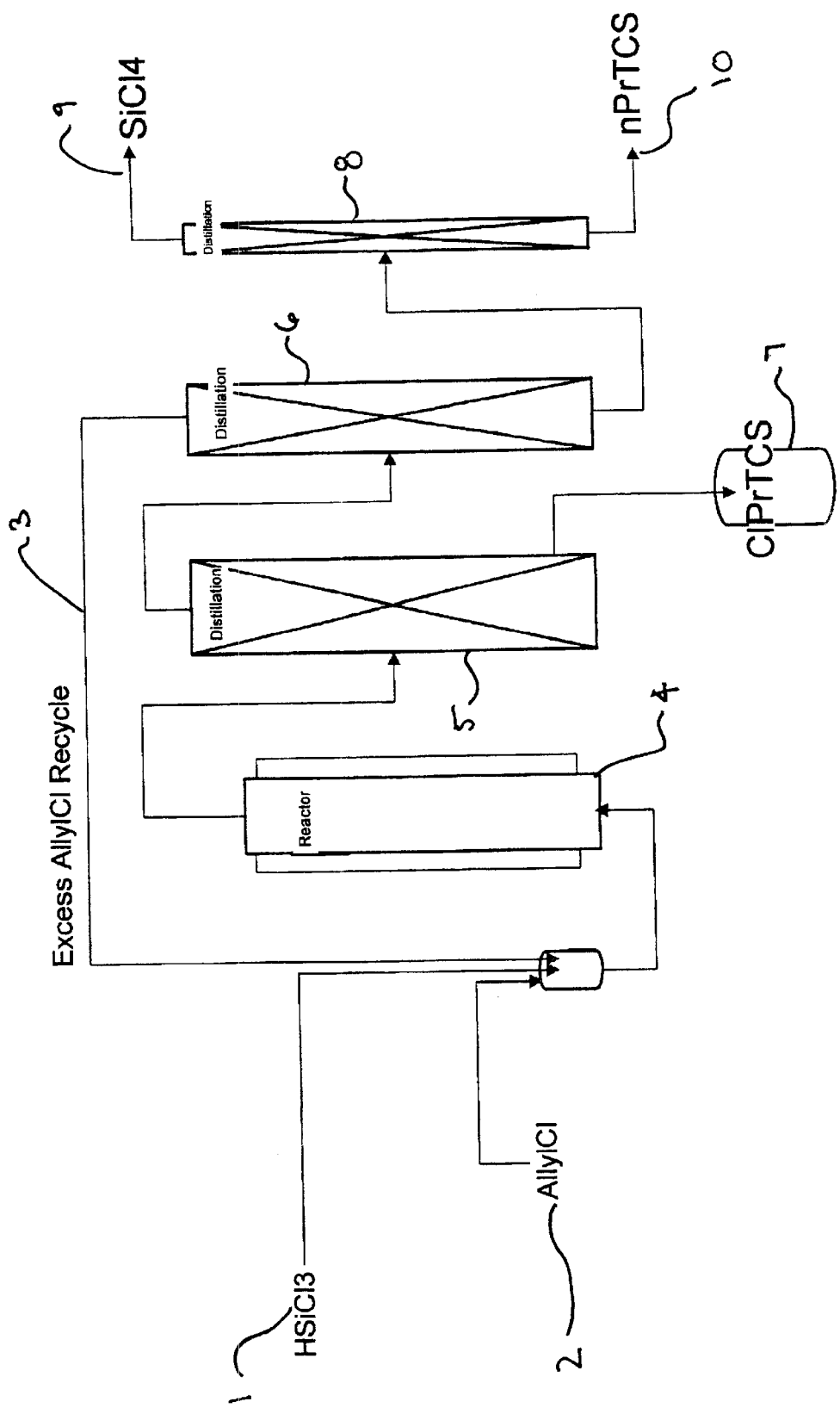
FIG. 1 is a flow diagram disclosing the process of a preferred embodiment of the present invention.

The present invention is a hydrosilation process that includes reacting an alkene halide with a hydrogen silane in the presence of a hydrosilating catalyst. The alkene halide is present in an amount such that a molar excess of at least 1.1 moles of alkene halide per mole of hydrogen silane is maintained.

Hydrogen silanes useful in the present process are described by formula $R_bX_aSiH_{4-a-b}$ where each $R_b$ is independently selected from the group consisting of alkyls comprising one to about 20 carbon atoms, cycloalkyls comprising about four to 12 carbon atoms, and aryls; a=0 to 3, b=0 to 3, and a+b=1 to 3. $R_b$ can be a substituted or unsubstituted alkyl, cycloalkyl, or aryl as described. It is preferred that each $R_b$ be independently selected from the group consisting of alkyls comprising one to about six carbon atoms. Even more preferred is when each $R_b$ is methyl. Each X is a halogen and preferably X is chlorine. Examples, of hydrogen silanes described by formula $R_bX_aSiH_{4-a-b}$ which may be useful in the present process include trimethylsilane, dimethylsilane, triethylsilane, dichlorosilane, trichlorosilane, methyidichlorosilane, dimethylchlorosilane, ethyldichlorosilane, cyclopentyldichlorosilane, methylphenylchlorosilane and (3,3,3-trifluoropropyl) dichlorosilane. Preferably, the hydrogen silane is selected from a group consisting of dimethylchlorosilane, methyldichlorosilane, trichlorosilane and dichlorosilane. Even more preferably the hydrogen silane is trichlorosilane.

Useful alkene halides may include, for example, vinyl chloride, allyl chloride, allyl bromide, allyl iodide, methallyl chloride, 3,3,3-trifluoropropene, 4-chloromethyl styrene, chloroprene and 4-chlorostyrene.

In a preferred embodiment, chloropropyltrichlorosilane is produced by reacting allyl chloride with trichlorosilane in the presence of a platinum containing catalyst. The allyl chloride is present in an amount of from such that a molar excess of from 1.1 moles of allyl chloride per mole of hydrogen silane to 50 moles of allyl halide per mole of hydrogen silane is maintained.

Even more preferably, the allyl chloride is present in an amount such that the molar excess is from 5 to 20 moles of allyl chloride per mole of hydrogen silane.

Unexpectedly, by maintaining at least a 5 mole excess of allyl chloride per mole trichlorosilane, the yield of the desired product, chloropropyltrichlorosilane is increased dramatically in relation to the undesired product, propyltrichlorosilane.

With reference to FIG. 1, there is detailed a process flow diagram for the process of the present invention. As can be seen from FIG. 1, the process includes providing allyl chloride and trichlorosilane into a reactor with subsequent separation steps to remove the reaction products as well as to recycle the excess allyl chloride.

The contacting of the allyl chloride with the trichlorosilane can be affected using suitable reactors including stirred vessels, loop reactors, and reactors for liquid solid contacts, such as a fixed bed reactor. The process may be run as a continuous, semi-continuous, or batch process. In a preferred embodiment, a fixed bed reactor is utilized to contact the liquid reactants with a solid platinum containing catalyst. The platinum containing catalyst is preferably a bimetallic catalyst of platinum and copper having a carbon support. The preferred catalyst is disclosed in U.S. Pat. No. 6,177,585 and is assigned to the assignee of the present invention and is herein incorporated by reference. The preferred catalyst includes an active hydrosilating metal, platinum, and a surface segregating metal, copper on a carbon support. Although a bimetallic catalyst is preferably utilized by the present invention, it is to be understood that other hydrosilating catalysts may be utilized by the present invention.

Again with reference to FIG. 1 the reactants, allyl chloride 1, trichlorosilane 2 and an allyl chloride recycle 3 are fed into a reactor 4, preferably a fixed bed reactor. The reactor has the preferred bimetallic catalyst as described above. The reactor temperature is maintained between 50° C. and 150° C. with a reaction pressure of from 100 to 250 psig. The reaction product is then subjected to a first separation stage 5, a distillation column, in which the desired product chloropropyltrichlorosilane 7 is separated as a bottom product.

The top product of the distillation is subjected to a subsequent separation stage 6 that separates the excess allyl chloride as a top product which is returned to the reactor 4 as a recycle stream 3. The bottom product of the second separation stage 6 is then subjected to a third separation 8 in which silicon tetrachloride 9 and propyltrichlorosilane 10 are separated for reuse in subsequent chemical processes or for disposal.

To reiterate, the liquid reactants are transferred to a reactor in which the liquids pass over a fixed bed of a platinum containing catalyst; thereby, producing the desired product, as well as an undesired secondary product. By increasing the allyl chloride reactant such that it is present in excess of at least 1.1 moles allyl chloride per mole trichlorosilane, the desired product yield is increased dramatically.

The following examples illustrate the present invention and will enable those skilled in the art to understand it in a more complete manner. It is to be understood that the invention is not limited to the particular examples detailed below.

TABLE 1

EXAMPLES

| Run | AllylCl Feed Rate, gm/hr | HSiCl3 Feed Rate, gm/hr | AllylCl/HSiCl3 Wt. Ratio | ClPrTCS/PrTCS Wt. Ratio |
| --- | --- | --- | --- | --- |
| 1 | 175.5 | 390 | 0.45 | 3.73 |
| 2 | 327.6 | 390 | 0.84 | 6.84 |
| 3 | 436.8 | 390 | 1.12 | 9.95 |
| 4 | 546 | 390 | 1.4 | 13.69 |
| 5 | 2187.9 | 390 | 5.61 | 27.37 |

As can be seen from the above table, a series of runs were completed utilizing a 1.58 inch ID tubular reactor containing 500 gm of a bimetallic platinum, copper catalyst. The catalyst was predried with nitrogen at 150° C. for 6 hours prior to use in the tubular reactor. After drying the catalyst, trichlorosilane was fed to the reactor at a rate of 390 m/hr while the allyl chloride feed rate was varied from 175 gm/hr to 2,187 gm/hr based on the specific run. The reactor temperature was maintained between 100° and 150° C. with a reaction pressure of from 150 to 250 psig. The crude reaction product was analyzed for product composition by utilizing an on-line gas chromatograph equipped with a thermal conductivity detector. The above table details the results of the reaction in terms of the weight ratio of the desired chloropropyltrichlorosilane to the undesired propyltrichlorosilane at various allyl chloride feed rates.

As can be seen from the detailed results, an increase in the allyl chloride feed rate corresponding to a 5.61 wt. ratio of allyl chloride to trichlorosilane, corresponding to an approximate 10 to 1 molar ratio, results in an approximate wt. ratio of 27 of the desired chloropropyltrichlorosilane to the undesired propyltrichlorosilane. This represents a three fold increase of the desired product to the undesired product over the third run, where an approximately 1 to 1 wt. ratio of feed, corresponding to an approximate 2 to 1 molar ratio of allyl chloride to trichlorosilane is utilized.

The present invention has been described in accordance with the relevant legal standards, thus the foregoing description is exemplary rather than limiting in nature. Variations and modifications to the disclosed embodiment may become apparent to those skilled in the art. Accordingly, the scope of legal protection afforded this invention can be determined by studying the following claims.

What is claimed is:

1. A process for producing an organosilane comprising:

reacting an alkene halide with a hydrogen silane in the presence of a bi-metallic metallic catalyst of platinum and copper having a carbon support, wherein the alkene halide and hydrogen silane are maintained in a liquid phase;

the alkene halide being present in an amount such that a molar excess of at least 1.1 moles per one mole of hydrogen silane is maintained and, wherein a reaction conversion of alkene halide and hydrogen silane is greater than 80 percent.

2. The process of claim 1 wherein the alkene halide is selected from the group consisting of: vinyl chloride, allyl chloride, allyl bromide, allyl iodide, methallyl chloride, 3,3,3-trifluoropropene,4-chloromethyl styrene, chloroprene and4-chlorostyrene.

3. The process of claim 1 wherein the hydrogen silane is described by formula $R_b X_a SiH_{4-a-b}$ where each $R_b$ is independently selected from the group consisting of alkyls comprising one to about 20 carbon atoms, cycloalkyls comprising about four to 12 carbon atoms, and aryls; a=0 to 3, b=0 to 3, and a+b=1 to 3 and $X_a$ is a halogen.

4. The process of claim 1 wherein the organosilane is chloropropyltrichlorosilane.

5. The process of claim 1 wherein the alkene halide comprises allyl chloride.

6. The process of claim 1 wherein the hydrogen silane comprises trichlorosilane.

7. The process of claim 1 wherein the hydrosilating catalyst comprises a platinum catalyst.

8. The process of claim 7 wherein the platinum catalyst comprises a bimetallic catalyst of platinum and copper having a carbon support.

9. The process of claim 1 wherein the alkene halide is present in an amount such that a molar excess of at least 10 moles per one mole of hydrogen silane is maintained.

10. The process of claim 4 wherein a weight ratio of a desired product, chloropropyltrichlorosilane over an undesired product, propyltrichlorosilane is at least 20.

11. A process for producing chloropropyltrichlorosilane comprising:

a) reacting allyl chloride with trichlorosilane in the presence of a bimetallic catalyst, wherein the allyl halide and trichlorosilane are maintained in a liquid phase; the allyl chloride being present in an amount such that a molar excess of at least 1.1 moles per one mole of trichlorosilane is maintained.

12. The process of claim 11 wherein the bimetallic catalyst comprises a platinum and copper catalyst having a carbon support.

13. The process of claim 11 wherein the reaction produces a desired product, chloropropyltrichlorosilane and an undesired product, propyltrichlorosilane and wherein a weight ratio of the desired product over the undesired product is at least 20.

14. The process of claim 11 wherein the allyl chloride is present in an amount such that a molar excess of at least 10 moles per one mole of trichlorosilane is maintained.

\* \* \* \* \*